United States Patent [19]
Kato et al.

[11] 3,936,460
[45] Feb. 3, 1976

[54] 1',4'-DIHYDRO-1-METHYL-SPIRO[PIPERIDINE AND PYROLIDINE-2,3'(2'H)QUINOLINE] COMPOUNDS

[75] Inventors: Hideo Kato; Eiichi Koshinaka, both of Fukui, Japan

[73] Assignee: Hokuriku Pharmaceutical Co., Ltd., Fukui, Japan

[22] Filed: Dec. 10, 1974

[21] Appl. No.: 531,322

[30] Foreign Application Priority Data
Dec. 19, 1973  Japan................................ 48-141178

[52] U.S. Cl. 260/288 CE; 260/288 CF; 260/289 K; 424/258
[51] Int. Cl.² ........................................ C07D 215/38
[58] Field of Search..... 260/288 CE, 288 CF, 289 K

[56] References Cited
OTHER PUBLICATIONS
Morrison et al., Organic Chemistry 2nd Edition, pp. 630–631, 1969.

*Primary Examiner*—Donald G. Daus
*Assistant Examiner*—Mary C. Vaughn
*Attorney, Agent, or Firm*—Burgess, Ryan and Wayne

[57] ABSTRACT

Spiro-compounds of the formula:

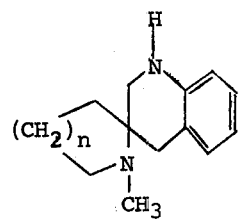

are disclosed. These compounds are useful as analgetic, antihistamine and spasmolytic agents. They are indicated in the management of conditions such as headache, seasonal allergies and the like.

3 Claims, No Drawings

1',4'-DIHYDRO-1-METHYL-SPIRO[PIPERIDINE AND PYROLIDINE-2,3'(2'H)QUINOLINE] COMPOUNDS

The present invention relates to novel spiro-compounds having pharmaceutical activities as well as novel processes for their production. More particularly, the present invention relates to novel spiro-compounds of the formula:

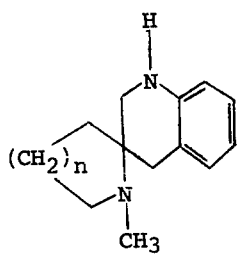

(I)

wherein $n$ stands for an integer 1 or 2, and the corresponding pharmaceutically acceptable acid addition salts.

According to the present invention, compound (I) can be prepared by treating a spiro-compound of the formula:

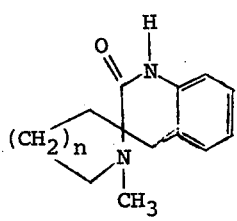

(II)

wherein $n$ is defined above, with a reducing agent. Lithium aluminum hydride can be employed as the reducing agent in the present invention. The preferred solvents for example include/anhydrous ether, tetrahydrofuran, dioxane, etc. The reaction is carried out preferably at temperatures of about boiling points of the solvent.

The products according to the present invention may be converted with an inorganic or organic acid into the corresponding salts by methods known in the art. Specific examples of the acids include hydrochloric acid, hydrobromic acid, oxalic acid, citric acid, tartaric acid, succinic acid, etc.

Starting compound (II) is disclosed in co-pending application Ser. No. 531,452 entitled "Novel Spiro-Compounds and Process Therefor," filed on Dec. 11, 1974.

Compound (I) and the salts thereof exhibit analgetic, anti-histamic and spasmolytic activities and vasoconstrictor effects on circulatory organs in a mammal. They are indicated in the management of conditions such as headache, minor muscular pain or seasonal allergies such as hay fever. A dose of 5 to 25 mg/kg orally or by injection 2 to 3 times daily is suggested. The dose regimen can be varied depending on the age, sex and weight of the patient by methods well known in the healing arts. Additionally, compound (I) is useful as an intermediate for the production of other pharmaceutical agents.

The invention will, now, be illustrated by the following examples:

Example 1

1', 4'-Dihydro-1-methyl-spiro[piperidine-2,3 (2'H)-quinoline].

To a suspension of $LiAlH_4$(0.1g) in 10ml $Et_2O$ was added dropwise a solution of 1',4'dihydro-1-methylspiro piperidine-2,3'-(2'H) quinoline-2'-one(0.1g) in $Et_2O$ with stirring and refluxed for 16 hours. The excess $LiAlH_4$ was decomposed with $H_2O$. The $Et_2O$ layer was decanted and the aqueous layer was extracted with $Et_2O$. The $Et_2O$ layers were combined, washed, dried and evaporated. The product obtained was recrystalized from iso-$Pr_2O$, mp.89°–90°.

Elemental Analysis $C_{14}H_{20}N_2$ Calcd. C:77.73; H:9.3; N:12.95; Found. C:77.56; H:9.37; N:12.79.

The following compound was obtained in a similar manner.

i. 1',4'-Dihydro-1-methyl-spiro [pyrrolidine-2,3'(-2'H)quinoline], mp. 100°–101°(Iso-$Pr_2O$)

What is claimed is:

1. A spiro-compound of the formula:

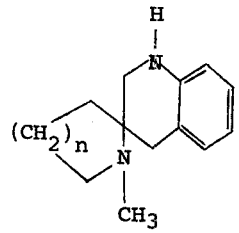

wherein $n$ stands for an integer of 1 or 2, and the corresponding pharmaceutically acceptable acid addition salts.

2. A compound according to claim 1 which is 1',4'-Dihydro-1-methyl-spiro [piperidine-2,3'(2'H)quinoline]

3. A compound according to claim 1 which is 1,4'-Dihydro-1methyl-spiro [pyrrolidine-2,3'(2'H)quinoline]

* * * * *

UNITED STATES PATENT OFFICE
CERTIFICATE OF CORRECTION

Patent No. 3,936,460   Dated February 3, 1976

Inventor(s) Hideo Kato, et al

It is certified that error appears in the above-identified patent and that said Letters Patent are hereby corrected as shown below:

In column 2, line 34: Change "150" to --iso--.

Signed and Sealed this first Day of June 1976

[SEAL]

Attest:

RUTH C. MASON
Attesting Officer

C. MARSHALL DANN
Commissioner of Patents and Trademarks